(12) United States Patent
Muhr

(10) Patent No.: US 6,333,429 B1
(45) Date of Patent: *Dec. 25, 2001

(54) PROCESS FOR PREPARING ALKALI METAL SALTS OF MALONIC MONOALKYL ESTERS

(75) Inventor: Juergen Muhr, Alfter (DE)

(73) Assignee: Degussa-Huels Aktiengesellschaft, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/621,090

(22) Filed: Jul. 21, 2000

(30) Foreign Application Priority Data

Jul. 21, 1999 (DE) ................................ 199 34 165

(51) Int. Cl.⁷ ........................... C07C 69/38; C07C 67/30
(52) U.S. Cl. .......................................... 560/190; 560/191
(58) Field of Search ............................................ 560/190

(56) References Cited

U.S. PATENT DOCUMENTS 6,172,257 * 1/2001 Muhr et al. ........................ 560/190

FOREIGN PATENT DOCUMENTS 198 17 101    10/1999    (DE) .
0 720 981    7/1996    (EP) .

OTHER PUBLICATIONS

J. van't Hoff, Ber. Dtsch. Chem. Ges., vol. 7, pp. 1570–1573, "Beiträge Zur Kenntniss Der Cyanessigsäure Und Malonsäure".

V.G.S. Box, et al., Heterocycles, vol. 32, No. 2, pp. 245–251, "The Synthesis of β–Lactones and β–Lactams from Malonates and Malonamides," 1991.

* cited by examiner

Primary Examiner—Gary Geist
Assistant Examiner—Zachary Tucker
(74) Attorney, Agent, or Firm—Oblon, Spivak, McClelland, Maier & Neustadt, P.C.

(57) ABSTRACT

The invention relates to a process for preparing alkali metal salts of malonic monoalkyl esters by selective saponification of malonic dialkyl esters using a basic alkali metal compound which comprises preparing from the malonic dialkyl ester and an alkali metal alkoxide, in a first stage, a CH-acid alkali metal salt of the malonic dialkyl ester and hydrolyzing this in a second stage by the action of water.

14 Claims, No Drawings

PROCESS FOR PREPARING ALKALI METAL SALTS OF MALONIC MONOALKYL ESTERS

BACKGROUND OF THE INVENTION

1. Field of the Invention

The invention relates to a process for preparing alkali metal salts of malonic monoalkyl esters by selective (or partial) saponification of malonic dialkyl esters via the intermediate of a CH-acid alkali metal salt.

2. Background of the Invention

Alkali metal salts of malonic monoalkyl esters and, in particular, potassium monoethyl malonate (abbreviated as KEM hereafter) are used as precursors for synthesizing pharmaceuticals having a quinolone structure. The use for syntheses in the pharmaceutical sector makes high demands on product purity.

A synthesis of potassium monoethyl malonate which was described as early as in the last century by van't Hoff (Ber. Dtsch. Chem. Ges., 7, 1572) and which is still currently practiced starts from diethyl malonate (abbreviated as DEM hereafter) which is selectively saponified with potassium hydroxide. According to EP 0 720 981 Al, this is performed using equimolar amounts of starting materials in an alcoholic medium, i.e. using alcoholic potassium hydroxide solution. However, the sought-after selective saponification is achieved only to an inadequate extent, so that only a target product which is considerably contaminated with dipotassium malonate (abbreviated as DKM below) is obtained. The DKM content is usually in the order of magnitude of several % by weight. Removal of the DKM from the KEM, which is necessary for use of the latter as a pharmaceutical precursor, is difficult and includes extensive purification operations.

Another disadvantage with said process is that alcoholic potassium hydroxide solution is not a customary commercial product, but must be prepared from alcohol and solid potassium hydroxide (caustic potash) with dissipation of the heat of solution. The handling and storage of caustic solids, such as caustic potash and caustic soda, in industrial amounts is associated with considerable costs for reasons of health and safety at work. In addition, alcoholic alkali metal hydroxide solutions, in particular those containing alcohols having a chain carbon number >1, generally cannot be stored without the initiation of aging processes which readily lead to product discoloration.

A further disadvantage of the known process is the relatively high dilution at which the process must be carried out. The alcohol is used at 19 to 28 times the amount by weight of potassium hydroxide. This large amount of alcohol has an adverse effect on the space-time yield and increases the expense for recovery of the solvent. The amount of alcohol is further increased by the DEM being used in alcoholic solution.

Box et al., Heterocycles, Vol. 32, No. 2, 1991, 245 ff., mention a synthesis of β-lactones and β-lactams, in which KEM acts as intermediate. In the experimental part, the preparation of KEM from DEM and alcoholic potassium hydroxide solution is described on page 247. The two starting materials are, as in the process of EP 0 720 981 Al already cited, used in equimolar amounts, that is to say each at 100 mmol. The molar ratios of DEM to KOH were calculated wrongly, however, since 20.225 g of DEM are 126 mmol and are equivalent to 1.26 times the molar amount of KOH. If it is further assumed that the potassium hydroxide used had, as is commercially usual, a KOH content of approximately 90% by weight (remainder water), 20.225 g of DEM are actually equivalent to 1.38 times the molar amount of KOH (calculated as 100%). Repeating the work using molar ratios of 1.26:1 and 1.38:1 showed that, although pure KEM containing less than 0.5% by weight of DKM is obtainable by this process, the precipitated KEM was very difficult to filter. In the case of laboratory batches, the filtering time was more than two hours. Such times are prohibitive for production on an industrial scale. In addition, according to Box et al., similarly to the case of the process of said EP 0 720 981 Al, considerable amounts of alcohol are required, and finally the yields of KEM are also not satisfactory.

German patent application 19817101.3 (O.Z. 5297) relates to a process for preparing KEM by selective saponification of DEM with potassium hydroxide, in which the potassium hydroxide is added to the DEM, DEM and potassium hydroxide are used in a molar ratio of at least 1.5 and the potassium hydroxide is distributed effectively in the DEM.

One of the objects of the present invention is to provide a process for preparing alkali metal salts of malonic monoalkyl esters which avoids said disadvantages of the prior art, i.e. without associated use of large amounts of alcohol and without using alcoholic alkali metal hydroxide solution, give high yields of pure low-DKM and readily filterable alkali metal salts of malonic monoalkyl esters. A further object of the invention is to provide a process which is similarly as advantageous as the process of said prior German patent application.

SUMMARY OF THE INVENTION

These objects are achieved according to the invention by a process for preparing alkali metal salts of malonic monoalkyl esters by selective saponification of malonic dialkyl esters using a basic alkali metal compound which comprises preparing from a malonic dialkyl ester and an alkali metal alkoxide, in a first stage, a CH-acid alkali metal salt of said malonic dialkyl ester and hydrolyzing this in a second stage by the action of water.

The process according to the invention may be described by the following formula:

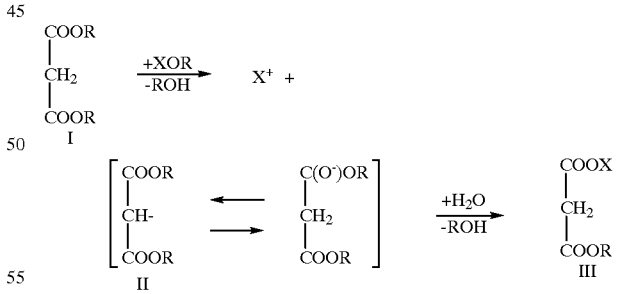

In this equation X is an alkali metal and R is an alkyl radical, advantageously containing from 1 to 4 carbon atoms. Preferably, R in the malonic dialkyl ester I has the same meaning as in the alkali metal alkoxide, since transesterifications are then prevented. The reaction product II of the first stage in which a mesomeric anion counteracts the cation $X^+$ is, for the purposes of this application, named as a CH-acid alkali metal salt of the malonic ester.

The process of the invention gives alkali metal salts of malonic monoalkyl esters III having a content of dialkali metal salts of malonic acid, such as DKM, of <1% by weight, and thus corresponds to the requirements for pharmaceutical syntheses. The process has acceptable filtration times and has a relatively low energy consumption for recovery of the alcohol and excess dialkyl malonate. In contrast to the process of the prior German application cited, not only KEM, but, according to the invention, other alkali metal salts of malonic monoethyl ester and the alkali metal salts of other malonic monoalkyl esters may also be prepared in high purity and in a highly filterable form. The process does not require a separate preparation of alcoholic alkali metal hydroxide solution from the alkali metal hydroxides and alcohol, but uses the alkali metal alkoxides which are available in the form of their alcoholic solutions in industrial amounts and are substantially stable to aging.

DETAILED DESCRIPTION OF THE PREFERRED EMBODIMENTS

An essential feature of the process of the invention comprises preparing, in a first stage, from a malonic dialkyl ester I and an alkali metal alkoxide a CH-acid alkali metal salt of the malonic dialkyl ester III. Preferred malonic dialkyl esters I are derived from alkanols having from 1 to 4 carbon atoms. Particular preference is given to the diethyl ester.

Preferred alkali metal alkoxides are the sodium alkoxides and, in particular, the potassium alkoxides. The alkali metal alkoxides are preferably used in the form of the from 10 to 30% by weight alcoholic solutions, as are prepared by reacting, with excess alcohol, alkali metal amalgams which are available in industrial amounts. It is also possible, in principle, to use solid alkali metal alkoxides. However, the advantage which solutions offer with respect to handling and metering is then lost.

Said starting materials can be used in equimolar amounts, but advantageously the malonic dialkyl ester I is used in up to 10-fold molar excess. Preference is given to a 0.5 to 1 0-fold, in particular a 2 to 4-fold, molar excess. The excess malonic dialkyl ester acts as an inert solvent or diluent. In addition, to the malonic dialkyl ester and/or the alcoholic alkali metal alkoxide solution can be added other inert solvents or diluents. Those which are suitable are, for example, aromatic or nonaromatic hydrocarbons, with or without inert substituents, such as toluene, the isomeric xylenes and ethylbenzene.

The process of the invention can be carried out, for example, in a stirred reactor or in a flow tube reactor. It is of no significance here in which sequence the starting materials are mixed with one another. Therefore, for example, the malonic dialkyl ester can be introduced into the alcoholic solution of the alkali metal alkoxide, the alcoholic alkali metal alkoxide solution can be passed into the malonic dialkyl ester, which may be dissolved in an inert solvent or diluent, or both starting materials can be simultaneously introduced into a flow reactor or into a stirred reactor into which some of the malonic dialkyl ester and/or an inert solvent or diluent had been charged.

The first stage of the process according to the invention is expediently carried out at atmospheric pressure and at a temperature of <80° C., preferably at <60° C., and in particular at from 0 to 30° C., advantageously with dissipation of the heat of reaction. The rate at which the CH-acid alkali metal salt II is formed depends, inter alia, on the reaction temperature and the alcohol component in the malonic dialkyl ester I and in the alkali metal alkoxide. Generally, the reaction proceeds spontaneously. The CH-acid salt precipitates out as a colorless solid, which is separated off from the reaction mixture, by filtration for example, and can be hydrolyzed in an inert solvent or diluent to give the target product. However, advantageously, separation is omitted and the hydrolysis is carried out right in the reaction mixture of the first stage, if appropriate—to improve the space-time yield—after removing all or some of the excess malonic dialkyl ester and/or inert solvent or diluent.

To prepare the alkali metal salt of the malonic monoalkyl ester III, in the second stage the CH-acid alkali metal salt II is hydrolyzed with water, advantageously with 1 to 5 mol, and in particular with about 1 mol, of water per mol of the alkali metal alkoxide used. The hydrolysis is expediently carried out at atmospheric pressure and at a temperature of <100° C., preferably <60° C., and in particular at from 0 to 40° C. The hydrolysis proceeds relatively rapidly and is generally completed in less than 5 hours. Longer hydrolysis times are possible, but are not associated with a particular advantage.

The colorless target product III is produced in solid form and can be separated off from the hydrolysis mixture in a conventional manner. It can be filtered without problems and may be further purified by extraction, e.g. using the alcohol of the corresponding ester. The wash liquid, the mother liquor and, if appropriate, the portions of the reaction mixture separated off by distillation downstream of the first stage can be used as starting material and reaction medium for a new batch after supplementation of the malonic dialkyl ester I consumed. However, expediently, at least some of the alcohol is separated off, in order to counteract an unwanted dilution of the reaction medium. This takes place advantageously under reduced pressure and/or with conjoint use of an entrainer which forms an azeotrope with the respective alcohol. Suitable entrainers are, for example, aliphatic and/or aromatic hydrocarbons, such as cyclohexane.

The present invention also provides for an improved method for preparing a pharmaceutical having a quinolone structure by using potassium monoethyl malonate, prepared by the above-described method, as a precursor.

The following examples are intended to illustrate the invention further, but not to restrict its field of application.

EXAMPLE 1

In the course of 1 h at 25° C. with stirring, 480.5 g (3 mol) of diethyl malonate (DEM) are added to 358.4 g (1 mol) of a 23.5% strength by weight solution of potassium ethoxide in ethanol. In the course of 1 h, 18.0 g (1 mol) of water are then added. The solid precipitated out is filtered off and washed twice, each time with 100 ml of ethanol, and dried in a water-pump vacuum. The KEM yield is 142.5 g (83.7%), the purity of which is >99%, determined by ion chromatography.

EXAMPLE 2

The procedure of example 1 is followed, but the diethyl malonate is initially charged and the potassium ethoxide solution added thereto. The KEM yield is 85% of theory, and the purity again >99%.

EXAMPLE 3

The procedure of example 1 is followed, but the filtrate is concentrated by distilling off the low-boilers in a low vacuum and is added to the next otherwise identical batch. The yield in the next batch is then >90% of theory, and the purity again >90%. This result continues to be achieved if the concentrated filtrate of one batch is added to the respective next batch.

This application is based on German patent application DE 19934165.6, filed with the German Patent Office on Jul. 21, 1999, the entire contents of which are hereby incorporated by reference.

What is claimed is:

1. A process for preparing an alkali metal salt of a malonic monoalkyl ester by selective saponification of a malonic dialkyl ester using a basic alkali metal compound which comprises
   i) reacting a malonic dialkyl ester and an alkali metal alkoxide to form a CH-acid alkali metal salt of said malonic dialkyl ester, wherein said malonic dialkyl ester and said alkali metal alkoxide are used in a molar ratio of from 1:1 to 10:1; and
   ii) hydrolyzing said CH-acid alkali metal salt by the action of water.

2. The process of claim 1, wherein step i) is carried out at a temperature of <80° C.

3. The process of claim 1, wherein step i) is carried out at a temperature of <60° C.

4. The process of claim 1, wherein step i) is carried out at a temperature of from 0 to 30° C.

5. The process of claim 1, wherein said hydrolysis is carried out at a temperature of <100° C.

6. The process as claim 1, wherein said hydrolysis is carried out a temperature of <60° C.

7. The process of claim 1, wherein said hydrolysis is carried out a temperature of from 0 to 40° C.

8. The process of claim 1, wherein said malonic dialkyl ester and said alkali metal alkoxide are used in a molar ratio of from 1.5:1 to 10:1.

9. The process of claim 1, wherein said malonic dialkyl ester and said alkali metal alkoxide are used in a molar ratio of from 2:1 to 4:1.

10. The process of claim 1, wherein a mother liquor obtained after separating off a solid alkali metal salt of said malonic monoalkyl ester are recirculated to step i) as starting material and reaction medium after supplementation of the malonic dialkyl ester consumed.

11. The process of claim 1, wherein a wash liquid after separation of alcohol and inert low-boiling solvent additionally introduced into said reaction recirculated to step i) as starting material and reaction medium after supplementation of the malonic dialkyl ester consumed.

12. The process of claim 1, wherein volatile reaction mixture constituents separated off downstream of step i) are recirculated to step i) as starting material and reaction medium after supplementation of the malonic dialkyl ester consumed.

13. A process for preparing an alkali metal salt of a malonic monoalkyl ester by selective saponification of a malonic dialkyl ester using a basic alkali metal compound which comprises
   i) reacting a malonic dialkyl ester and an alkali metal alkoxide to form a CH-acid alkali metal salt of said malonic dialkyl ester, wherein said malonic dialkyl ester and said alkali metal alkoxide are used in a molar ratio of from 1.5:1 to 10:1; and
   ii) hydrolyzing said CH-acid alkali metal salt by the action of water.

14. A process for preparing an alkali metal salt of a malonic monoalkyl ester by selective saponification of a malonic dialkyl ester using a basic alkali metal compound which comprises
   i) reacting a malonic dialkyl ester and an alkali metal alkoxide to form a CH-acid alkali metal salt of said malonic dialkyl ester, wherein said malonic dialkyl ester and said alkali metal alkoxide are used in a molar ratio of from 2:1 to 4:1; and
   ii) hydrolyzing said CH-acid alkali metal salt by the action of water.

* * * * *